United States Patent
Hawkins et al.

(10) Patent No.: US 8,719,046 B2
(45) Date of Patent: May 6, 2014

(54) SYSTEMS AND METHODS FOR INTERRUPTION WORKFLOW MANAGEMENT

(75) Inventors: Michael Hawkins, Hoboken, NJ (US); Christopher Burt, Warwick, NY (US); Kenneth Lopez, New York, NY (US); Jason Klotzer, Woodside, NY (US); Andres Olivares, Hackettstown, NJ (US); Natalia Lipetskaia, Jersey City, NJ (US)

(73) Assignee: General Electric Company, Schenectady, NY (US)

( * ) Notice: Subject to any disclaimer, the term of this patent is extended or adjusted under 35 U.S.C. 154(b) by 482 days.

(21) Appl. No.: 12/323,046

(22) Filed: Nov. 25, 2008

(65) Prior Publication Data

US 2010/0131292 A1    May 27, 2010

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ....................................................... 705/2–3
See application file for complete search history.

(56) References Cited

U.S. PATENT DOCUMENTS

| | | | |
|---|---|---|---|
| 5,748,907 A * | 5/1998 | Crane | 705/2 |
| 7,027,997 B1 * | 4/2006 | Robinson et al. | 705/7.26 |
| 2003/0220815 A1 * | 11/2003 | Chang et al. | 705/2 |
| 2004/0172291 A1 * | 9/2004 | Knowlton | 705/2 |
| 2006/0247948 A1 * | 11/2006 | Ellis et al. | 705/2 |

OTHER PUBLICATIONS

Microsoft Project, Microsoft Office Project Professional 2003, 2003.*

* cited by examiner

*Primary Examiner* — Tran Nguyen
(74) *Attorney, Agent, or Firm* — Hanley, Flight and Zimmerman, LLC

(57) ABSTRACT

Certain embodiments of the present invention provide systems and methods for interruption workflow management in a clinical enterprise. Certain embodiments provide an interruption workflow management system for a clinical enterprise. The system includes a worklist including a plurality of patient indicators representing patients for which tasks are to be performed by a user. The system also includes a patient panel displaying patient information associated with a patient indicator selected from the worklist. The system further includes a patient indicator shelf holding one or more patient indicators from at least one of the worklist and the patient panel for later retrieval in response to user input. The patient indicator shelf facilitates restoration of a patient indicator from the patient indicator shelf to display in the patient panel in response to user input.

18 Claims, 6 Drawing Sheets

SYSTEMS AND METHODS FOR INTERRUPTION WORKFLOW MANAGEMENT

BACKGROUND OF THE INVENTION

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

PACS were initially used as an information infrastructure supporting storage, distribution, and diagnostic reading of images acquired in the course of medical examinations. As PACS developed and became capable of accommodating vast volumes of information and its secure access, PACS began to expand into the information-oriented business and professional areas of diagnostic and general healthcare enterprises. For various reasons, including but not limited to a natural tendency of having one information technology (IT) department, one server room, and one data archive/backup for all departments in healthcare enterprise, as well as one desktop workstation used for all business day activities of any healthcare professional, PACS is considered as a platform for growing into a general IT solution for the majority of IT oriented services of healthcare enterprises.

Medical imaging devices now produce diagnostic images in a digital representation. The digital representation typically includes a two dimensional raster of the image equipped with a header including collateral information with respect to the image itself, patient demographics, imaging technology, and other data used for proper presentation and diagnostic interpretation of the image. Often, diagnostic images are grouped in series each series representing images that have some commonality and differ in one or more details. For example, images representing anatomical cross-sections of a human body substantially normal to its vertical axis and differing by their position on that axis from top (head) to bottom (feet) are grouped in so-called axial series. A single medical exam, often referred as a "study" or an "exam" typically includes one or more series of images, such as images exposed before and after injection of contrast material or images with different orientation or differing by any other relevant circumstance(s) of imaging procedure. The digital images are forwarded to specialized archives equipped with proper means for safe storage, search, access, and distribution of the images and collateral information for successful diagnostic interpretation.

Diagnostic physicians that read a study digitally via access to a PACS from a local workstation currently suffer from a significant problem associated with the speed of study opening and making studies available for review where the reading performance of some radiologists requires opening up to 30 MRI studies an hour. Currently, a significant portion of a physician's time is spent just opening the study at the local workstation. When a user is reading one study after another, a switch from a study just read to the next study to be read requires two mouse clicks (one to close the current study and one to open the next study via the physician worklist), introduces delay between those clicks necessary for the refresh of the study list, and an additional delay for loading the next study.

BRIEF SUMMARY OF THE INVENTION

Certain embodiments of the present invention provide systems and methods for interruption workflow management in a clinical enterprise.

Certain embodiments provide a method for interruption workflow management via a workstation in a clinical enterprise. The method includes generating a worklist for a user including a plurality of patient tasks to be performed by that user, the patients represented in the worklist using a patient indicators. The method also includes displaying patient information associated with a patient indicator selected from the worklist in an active patient area. The method further includes moving the patient indicator from the active patient area to a patient indicator shelf for later retrieval in response to user input. Additionally, the method includes restoring the patient indicator from the patient indicator shelf to the active patient area in response to user input.

Certain embodiments provide an interruption workflow management system for a clinical enterprise. The system includes a worklist including a plurality of patient indicators representing patients for which tasks are to be performed by a user. The system also includes a patient panel displaying patient information associated with a patient indicator selected from the worklist. The system further includes a patient indicator shelf holding one or more patient indicators from at least one of the worklist and the patient panel for later retrieval in response to user input. The patient indicator shelf facilitates restoration of a patient indicator from the patient indicator shelf to display in the patient panel in response to user input.

Certain embodiments provide a machine readable medium having a set of instructions for execution on a computing machine, which, when executed, cause the computing machine to execute a method for interruption workflow management via a workstation in a clinical enterprise. The method includes generating a worklist for a user including a plurality of patient tasks to be performed by that user, the patients represented in the worklist using a patient indicators.

The method also includes displaying patient information associated with a patient indicator selected from the worklist in an active patient area. The method further includes moving the patient indicator from the active patient area to a patient indicator shelf for later retrieval in response to user input. Additionally, the method includes restoring the patient indicator from the patient indicator shelf to the active patient area in response to user input.

Figure 1:
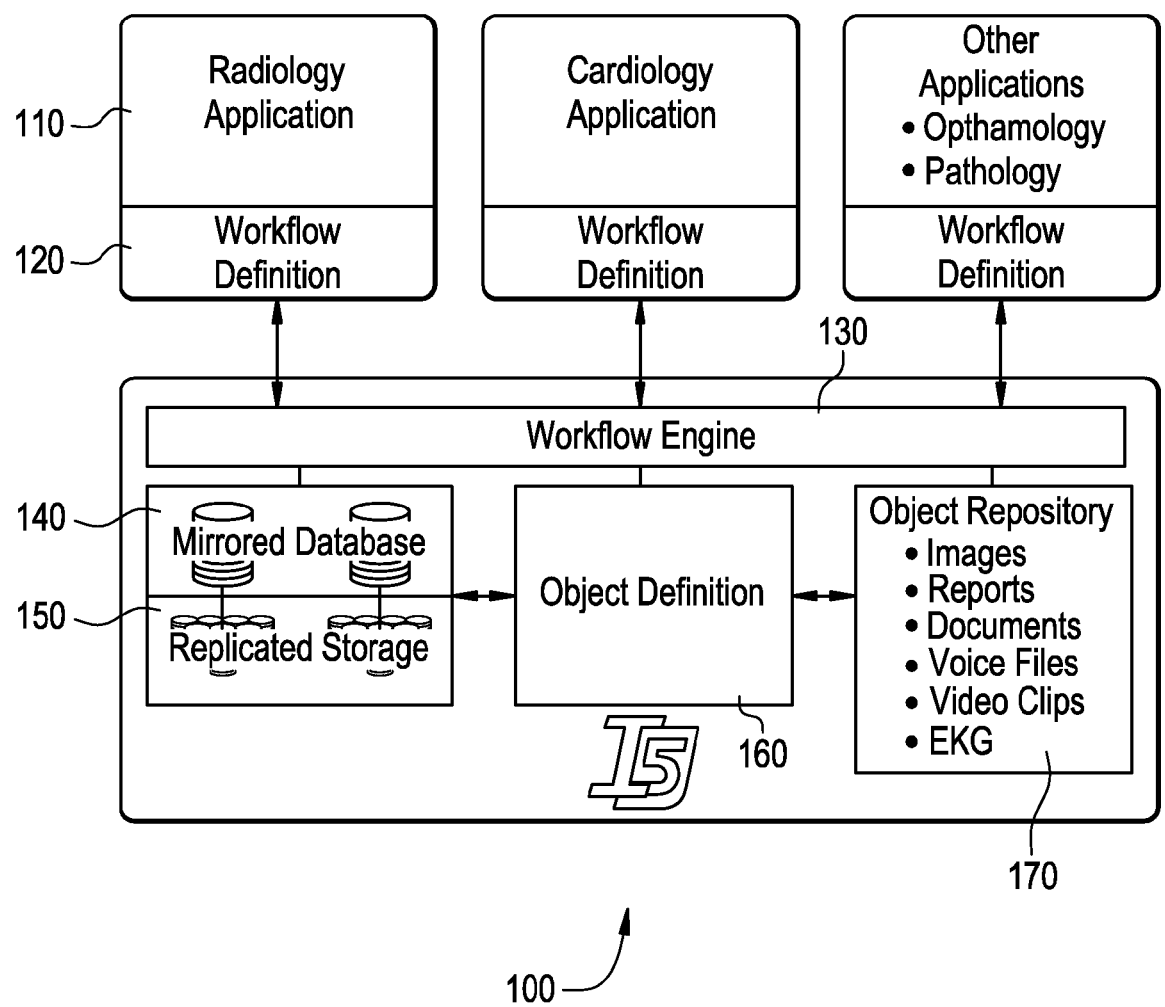
FIG. 1 demonstrates a business and application diagram for PACS information system in accordance with certain embodiments of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments address user workflow management and accommodation of user multi-tasking and interruption. In a typical clinical environment, a user is frequently interrupted. Certain embodiments allow a user to keep track of what he or she was doing (e.g., bookmark items) so that the user can go back to bookmarked items and access them again, including dictations, annotations, downloaded images (e.g., making sure that the images the user downloaded are still downloaded), etc. For example, a user downloads a large computed tomography ("CT") study, then looks at a small computed radiography ("CR") study, and wants to make sure that the CT images are still on the clinical information system including any annotations he or she was making. Also, a user may need to get up and physically move from a first workstation to another workstation and may lose his or her spot in review on the first workstation. Therefore, example systems and methods enable persistence between different work items and also between different sessions, different workstations, etc.

A bookmark might be created and saved for a short term and/or a long term. For example, a user may create a bookmark because items relate to a patient for whom the physician is seeking a consultation. For example, a physician reviews a patient's CT exam and indicates that the patient needs emergency surgery. The physician saves or bookmarks the patient all day because the physician expects a surgeon is going to call regarding the procedure as well as a nurse and/or primary physician, for example. By setting aside and saving the information for that patient, the user can move on in his or her workflow without worrying about lost information.

Similarly, bookmarks can be beneficial for a technician managing multiple scans.

As another example, for referring clinicians doing rounds, a resident doesn't know when an attending is going to have time to review cases. As soon as he or she sees the attending, the resident can log in and see all the patients on his or her shelf (e.g., patient bookmarks or placeholder reminders). A patient flash card space on the side of the interface display enables a user to send what he or she is reading to the shelf but also allows the user to jump ahead and jump back in the user's workflow. Information can follow from session to session, location to location, day to day, for example. For example, if a user sees a good teaching case, he or she can set that case aside for days until he or she has time to forward it to other residents.

In certain embodiments, a user can drag a patient card from his or her worklist to a bookmark shelf and can configure to keep the patient in the worklist also or can remove the patient card so that it remains on the shelf For example, a user's worklist could include only unread items, and the user's patient shelf could be configured to require a reason associated with putting a patient there. For example, suppose there is a CR image series of a chest that gave a coronal view, but a reviewer wants a sagittal view. The reviewer can put the image series for the patient on his or her shelf with an associated reason being to obtain an additional view. The reviewer can bring the item off of the shelf and into an active patient area of his or her interface once the additional sagittal view has been provided. An all unread items worklist can exclude items that have an uncompleted reason code, for example. An administrator can have access to see all items on the shelf As an option, a color and/or other indicator for items sitting on the shelf can change depending upon how long an item has been sitting on the shelf.

In an example, on a left side of a user's graphical interface workspace, a user can see a list of patients of his or her patients without having to go back to another workspace and can easily switch between patients. A patient card provides a summary of an entire patient record, patient priority, patient and procedure demographics, key identification information, graphical indicator of priority, etc. For example, the patient card gives a snapshot of that patient. Priority options can be defined for patient cards in the user's worklist. Icons on the patient card can be used to define how information for the patient (e.g., an imaging study) have been made available (e.g., full or partial streaming to the user from a server, fully or partially available locally on the hard drive, available in hard copy film, available for prefetch, etc.). Icons and/or other indicators can indicate whether the user locked a workflow, whether a user has access, etc.

In an example, if a user is working on one patient and another comes in with a stat priority, the user can set the first patient on the workspace shelf and set that patient aside to look at the second patient. The user can then pull the first patient back off of the shelf from within the application rather than via a separate instance on the user's desktop. In certain embodiments, if a user logs out of or exits a session, the shelf persists with its stored patient information. A user can set a patient on the shelf while the user is waiting for other views from a technician, for example, and can go on to another patient.

Certain embodiments can be used for scheduling, registration, etc. Certain embodiments provide interaction between a workflow/worklist of patients and a shelf or holding area of patients as information comes in and is acted upon by one or more users. One or more authorized users/administrators can review and analyze items waiting on a shelf. Certain embodiments facilitate data mining based on shelf content (e.g., how often are doctors requesting additional views, what types of patients are waiting on the shelf, what departments are users waiting on via the shelf, etc.). Certain embodiments provide related business intelligence and system intelligence information to generate metrics, for example.

Certain embodiments provide "at hand" access to new work as it reaches a user's queue. Certain embodiments provide an ability to save a shelved item until its work is completed, across sessions and workstations. Certain embodiments provide an ability to maintain multiple simultaneous work items. An organization and workflow are provided to allow a user to review a pending list of patients via patient cards as well as a shelf of saved patients pending further action.

Certain embodiments operate in conjunction with one or more information systems for a healthcare enterprise including a PACS system for radiology and/or other subspecialty system as demonstrated by the business and application diagram in FIG. 1. The system 100 of FIG. 1 includes a clinical application 110, such as a radiology, cardiology, ophthalmology, pathology, and/or application. The system 100 also includes a workflow definition 120 for each application 110. The workflow definitions 120 communicate with a workflow engine 130. The workflow engine 130 is in communication with a mirrored database 140, object definitions 60, and an object repository 170. The mirrored database 140 is in communication with a replicated storage 150. The object repository 170 includes data such as images, reports, documents, voice files, video clips, EKG information, etc.

Figure 2:
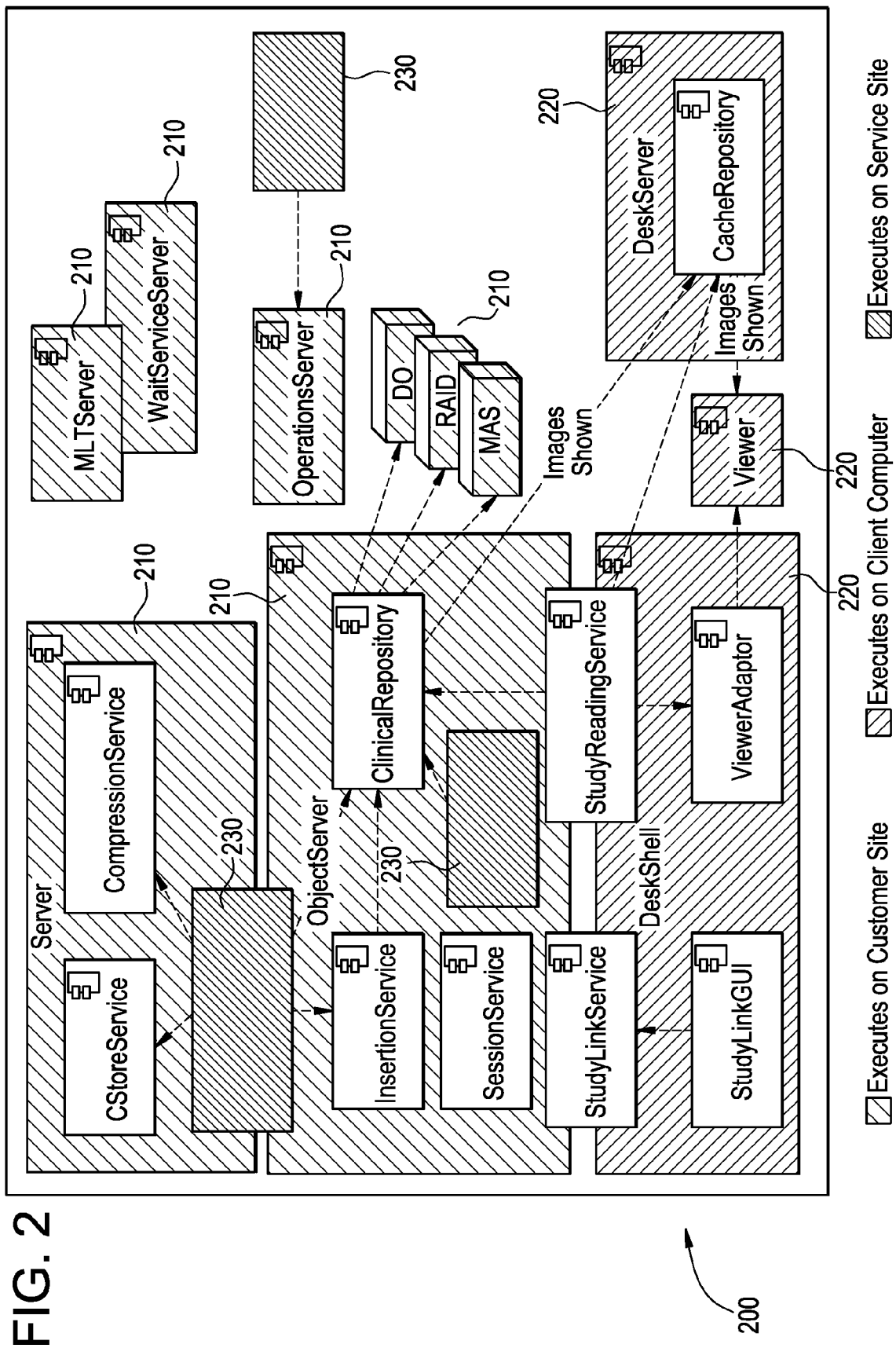
FIG. 2 illustrates certain embodiments of an information system delivering application and business content in accordance with an embodiment of the present invention.

An embodiment of an information system that delivers application and business goals is presented in FIG. 2. The specific arrangement and contents of the assemblies constituting this embodiment bears sufficient novelty and constitute part of certain embodiments of the present invention. The information system 200 of FIG. 2 demonstrates services divided among a service site 230, a customer site 210, and a client computer 220. For example, a Dicom Server, HL7 Server, Web Services Server, Operations Server, database and other storage, an Object Server, and a Clinical Repository execute on a customer site 210. A Desk Shell, a Viewer, and a Desk Server execute on a client computer 220. A Dicom Controller, Compiler, and the like execute on a service site 230. Thus, operational and data workflow may be divided, and only a small display workload is placed on the client computer 220, for example.

Certain embodiments provide an architecture and framework for a variety of clinical applications. The framework can include front-end components including but not limited to a Graphical User Interface ("GUI") and can be a thin client and/or thick client system to varying degree, which some or all applications and processing running on a client workstation, on a server, and/or running partially on a client workstation and partially on a server, for example.

Figure 3:
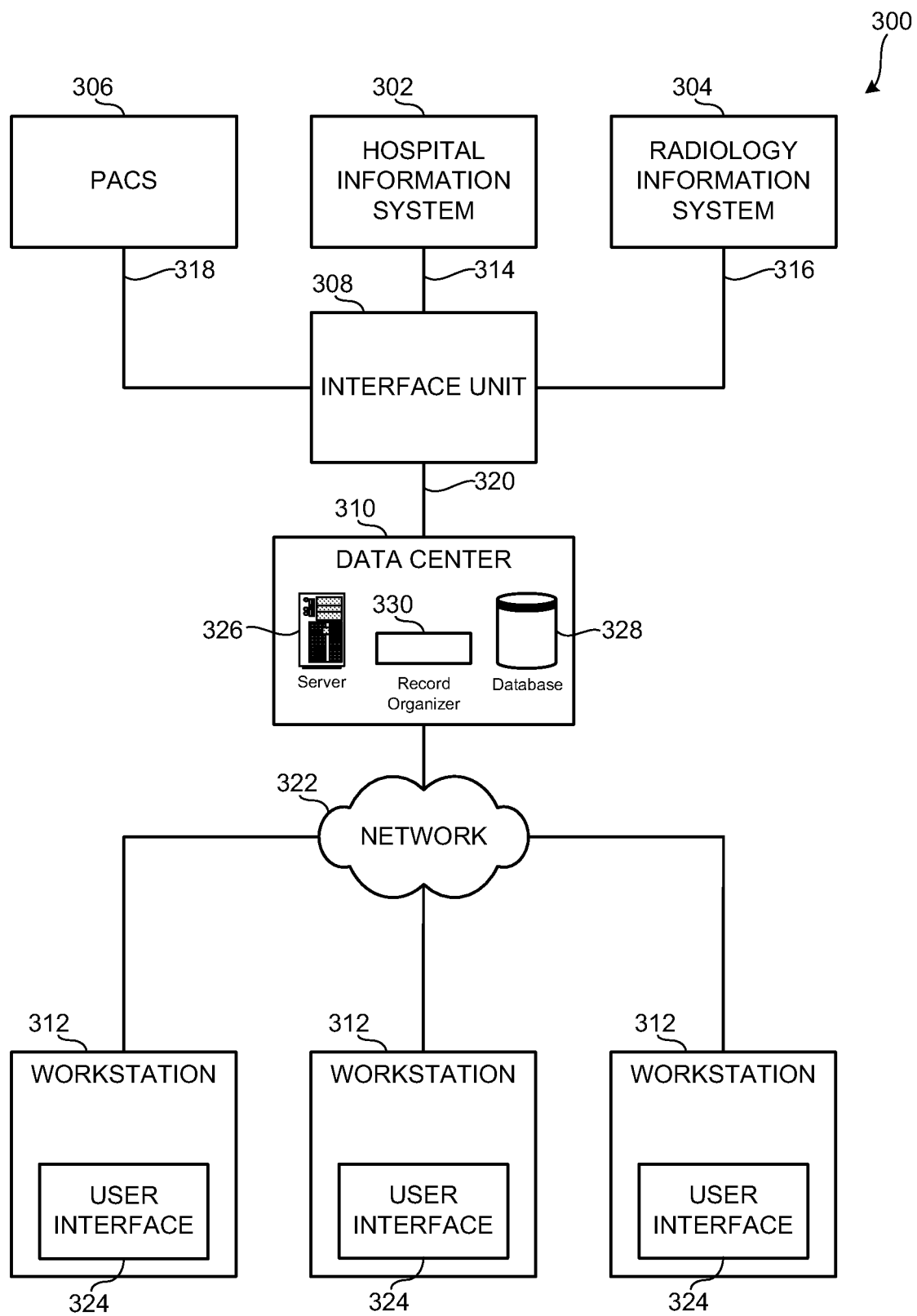
FIG. 3 illustrates a block diagram of an example clinical information system that may be used to implement systems and methods described herein.

FIG. 3 shows a block diagram of an example clinical information system 300 capable of implementing the example methods and systems described herein. The example clinical information system 300 includes a hospital information system ("HIS") 302, a radiology information system ("RIS") 304, a picture archiving and communication system ("PACS") 306, an interface unit 308, a data center 310, and a plurality of workstations 312. In the illustrated example, the HIS 302, the RIS 304, and the PACS 306 are housed in a healthcare facility and locally archived. However, in other implementations, the HIS 302, the RIS 304, and/or the PACS 306 may be housed one or more other suitable locations. In certain implementations, one or more of the PACS 306, RIS 304, HIS 302, etc., can be implemented remotely via a thin client and/or downloadable software solution. Furthermore, one or more components of the clinical information system 300 may be combined and/or implemented together. For example, the RIS 304 and/or the PACS 306 may be integrated with the HIS 302; the PACS 306 may be integrated with the RIS 304; and/or the three example information systems 302, 304, and/or 306 may be integrated together. In other example implementations, the clinical information system 300 includes a subset of the illustrated information systems 302, 304, and/or 306. For example, the clinical information system 300 may include only one or two of the HIS 302, the RIS 304, and/or the PACS 306. Preferably, information (e.g., scheduling, test results, observations, diagnosis, etc.) is entered into the HIS 302, the RIS 304, and/or the PACS 306 by healthcare practitioners (e.g., radiologists, physicians, and/or technicians) before and/or after patient examination.

The HIS 302 stores medical information such as clinical reports, patient information, and/or administrative information received from, for example, personnel at a hospital, clinic, and/or a physician's office. The RIS 304 stores information such as, for example, radiology reports, messages, warnings, alerts, patient scheduling information, patient demographic data, patient tracking information, and/or physician and patient status monitors. Additionally, the RIS 304 enables exam order entry (e.g., ordering an x-ray of a patient) and image and film tracking (e.g., tracking identities of one or more people that have checked out a film). In some examples, information in the RIS 304 is formatted according to the HL-7 (Health Level Seven) clinical communication protocol.

The PACS 306 stores medical images (e.g., x-rays, scans, three-dimensional renderings, etc.) as, for example, digital images in a database or registry. In some examples, the medical images are stored in the PACS 306 using the Digital Imaging and Communications in Medicine ("DICOM") format. Images are stored in the PACS 306 by healthcare practitioners (e.g., imaging technicians, physicians, radiologists) after a medical imaging of a patient and/or are automatically transmitted from medical imaging devices to the PACS 306 for storage. In some examples, the PACS 306 may also include a display device and/or viewing workstation to enable a healthcare practitioner to communicate with the PACS 306.

The interface unit 308 includes a hospital information system interface connection 314, a radiology information system interface connection 316, a PACS interface connection 318, and a data center interface connection 320. The interface unit 308 facilities communication among the HIS 302, the RIS 304, the PACS 306, and/or the data center 310. The interface connections 314, 316, 318, and 320 may be implemented by, for example, a Wide Area Network ("WAN") such as a private network or the Internet. Accordingly, the interface unit 308 includes one or more communication components such as, for example, an Ethernet device, an asynchronous transfer mode ("ATM") device, an 802.11 device, a DSL modem, a cable modem, a cellular modem, etc. In turn, the data center 310 communicates with the plurality of workstations 312, via a network 322, implemented at a plurality of locations (e.g., a hospital, clinic, doctor's office, other medical office, or terminal, etc.). The network 322 is implemented by, for example, the Internet, an intranet, a private network, a wired or wireless Local Area Network, and/or a wired or wireless Wide Area Network. In some examples, the interface unit 308 also includes a broker (e.g., a Mitra Imaging's PACS Broker) to allow medical information and medical images to be transmitted together and stored together.

In operation, the interface unit 308 receives images, medical reports, administrative information, and/or other clinical information from the information systems 302, 304, 306 via the interface connections 314, 316, 318. If necessary (e.g., when different formats of the received information are incompatible), the interface unit 308 translates or reformats (e.g., into Structured Query Language ("SQL") or standard text) the medical information, such as medical reports, to be properly stored at the data center 310. Preferably, the reformatted medical information may be transmitted using a transmission protocol to enable different medical information to share common identification elements, such as a patient name or social security number. Next, the interface unit 308 transmits the medical information to the data center 310 via the data center interface connection 320. Finally, medical information is stored in the data center 310 in, for example, the DICOM format, which enables medical images and corresponding medical information to be transmitted and stored together.

The medical information is later viewable and easily retrievable at one or more of the workstations 312 (e.g., by their common identification element, such as a patient name or record number). The workstations 312 may be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 312 receive commands and/or other input from a user via, for example, a keyboard, mouse, track ball, microphone, etc. As shown in FIG. 3, the workstations 312 are connected to the network 322 and, thus, can communicate with each other, the data center 310, and/or any other device coupled to the network 322. The workstations 312 are capable of implementing a user interface 324 to enable a healthcare practitioner to interact with the clinical information system 300. For example, in response to a request from a physician, the user interface 324 presents a patient medical history. Additionally, the user interface 324 includes one or more options related to the example methods and apparatus described herein to organize such a medical history using classification and severity parameters.

The example data center 310 of FIG. 3 is an archive to store information such as, for example, images, data, medical reports, and/or, more generally, patient medical records. In addition, the data center 310 may also serve as a central conduit to information located at other sources such as, for example, local archives, hospital information systems/radiology information systems (e.g., the HIS 302 and/or the RIS 304), or medical imaging/storage systems (e.g., the PACS 306 and/or connected imaging modalities). That is, the data center 310 may store links or indicators (e.g., identification numbers, patient names, or record numbers) to information. In the illustrated example, the data center 310 is managed by an application server provider ("ASP") and is located in a centralized location that may be accessed by a plurality of systems and facilities (e.g., hospitals, clinics, doctor's offices, other medical offices, and/or terminals). In some examples, the data center 310 may be spatially distant from the HIS 302, the RIS 304, and/or the PACS 306 (e.g., at General Electric® headquarters).

The example data center 310 of FIG. 3 includes a server 326, a database 328, and a record organizer 330. The server 326 receives, processes, and conveys information to and from the components of the clinical information system 300. The database 328 stores the medical information described herein and provides access thereto. The example record organizer 330 of FIG. 3 manages patient medical histories, for example. The record organizer 330 can also assist in procedure scheduling, for example.

Figure 4:
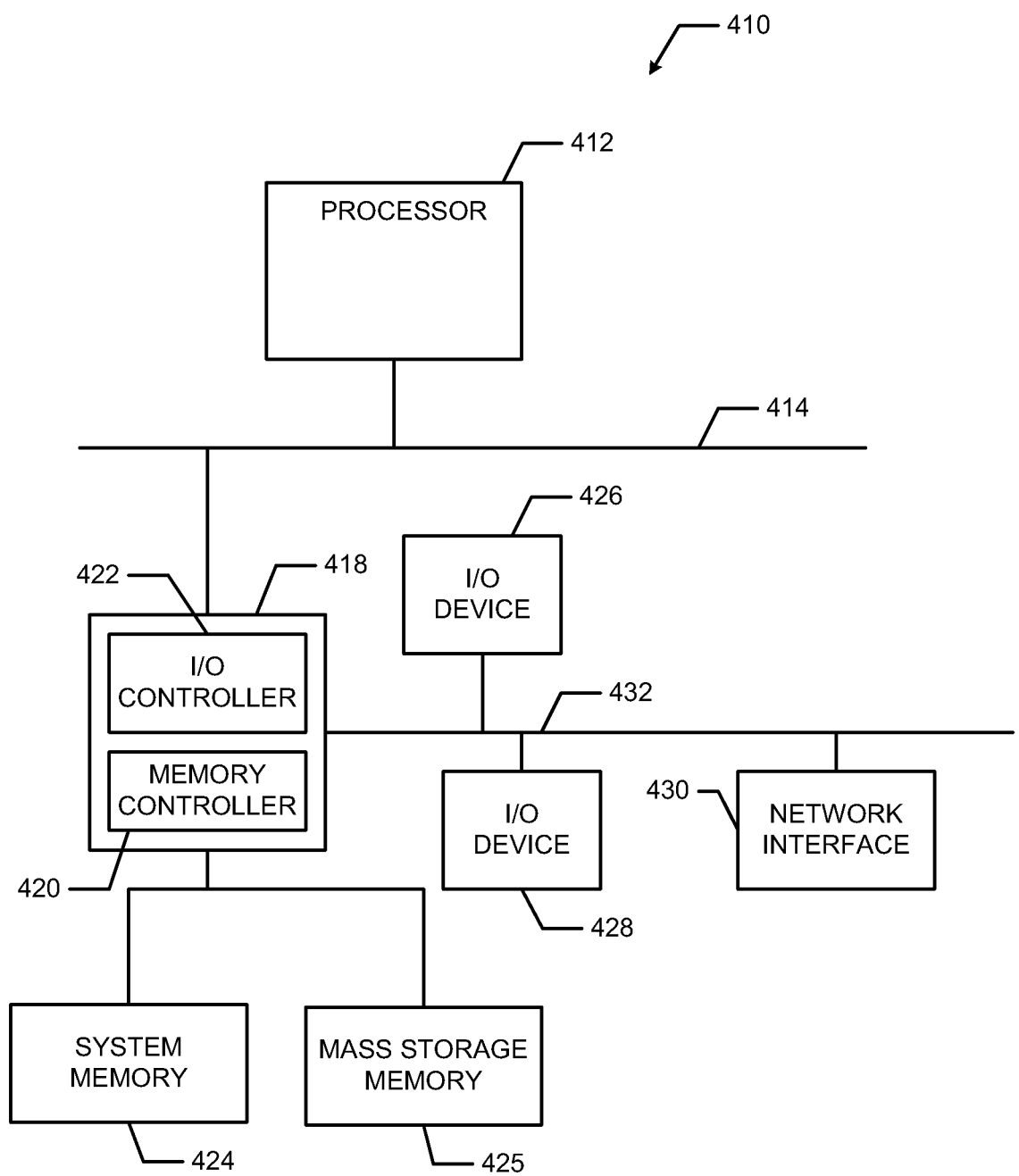
FIG. 4 shows a block diagram of an example processor system that may be used to implement systems and methods described herein.

FIG. 4 is a block diagram of an example processor system 410 that may be used to implement systems and methods described herein. As shown in FIG. 4, the processor system 410 includes a processor 412 that is coupled to an interconnection bus 414. The processor 412 may be any suitable processor, processing unit, or microprocessor, for example. Although not shown in FIG. 4, the system 410 may be a multi-processor system and, thus, may include one or more additional processors that are identical or similar to the processor 412 and that are communicatively coupled to the interconnection bus 414.

The processor 412 of FIG. 4 is coupled to a chipset 418, which includes a memory controller 420 and an input/output ("I/O") controller 422. As is well known, a chipset typically provides I/O and memory management functions as well as a plurality of general purpose and/or special purpose registers, timers, etc. that are accessible or used by one or more processors coupled to the chipset 418. The memory controller 420 performs functions that enable the processor 412 (or processors if there are multiple processors) to access a system memory 424 and a mass storage memory 425.

The system memory 424 may include any desired type of volatile and/or non-volatile memory such as, for example, static random access memory (SRAM), dynamic random access memory (DRAM), flash memory, read-only memory (ROM), etc. The mass storage memory 425 may include any desired type of mass storage device including hard disk drives, optical drives, tape storage devices, etc.

The I/O controller 422 performs functions that enable the processor 412 to communicate with peripheral input/output ("I/O") devices 426 and 428 and a network interface 430 via an I/O bus 432. The I/O devices 426 and 428 may be any desired type of I/O device such as, for example, a keyboard, a video display or monitor, a mouse, etc. The network interface 430 may be, for example, an Ethernet device, an asynchronous transfer mode ("ATM") device, an 802.11 device, a DSL modem, a cable modem, a cellular modem, etc. that enables the processor system 410 to communicate with another processor system.

While the memory controller 420 and the I/O controller 422 are depicted in FIG. 4 as separate blocks within the chipset 418, the functions performed by these blocks may be integrated within a single semiconductor circuit or may be implemented using two or more separate integrated circuits.

According to certain embodiments considered as examples in the present application, certain media files imported from a medical imaging device into a PACS are grouped in sequences called series, and certain series are grouped into studies, where each study represents a total set of media associated with a single medical exam. Each such study can be optionally attributed to a study type, where each study type is associated with a certain protocol for study interpretation. The protocol can include but is not limited to an order and positions for series display, configuration of a toolbar, annotation and measuring tools, and/or other data required for more efficient presentation of diagnostic images and rendering of a diagnosis. The set of tools and resources is referred to as a "study layout."

For each study registered in the database, an algorithm (e.g., a unique algorithm) exists for creation of a list of respective series and individual images included in the study and selection of a proper layout for study display. Upon getting a request for study display, the server first generates comprehensive lists of media files to be used for reading the study and a related layout for study display. These lists are transferred to a client workstation and copies are kept on the server. According to the generated list of media files and a chosen layout for their presentation on the client workstation, a plan for transferring and optional processing and/or decompression of the media files is built and coordinated between client and server.

A workflow includes a series of tasks executed to achieve a desired goal. A rule-based workflow system is one whose behavior is codified for particular business data and events. Computer supported cooperative work ("CSCW") is software designed to allow a group of users on a network to work simultaneously on a project. Groupware can provide services for communicating (e.g., email, text messaging, etc.), group document development, scheduling, and tracking, for example.

In an example digital workflow, a physician order entry ("POE") is created for a magnetic resonance ("MR") imaging exam on a specific patient. The workflow includes user authentication, selection of POE order, selection of the patient, and selection of the exam. The workflow further includes entering a clinical indication, entering signs and symptoms, and answering MR safety screening questions to determine priority of exam. The workflow includes reviewing and finalizing of the POE order. In order to define the workflow, a user can define what information must be provided by a referring physician in the POE. For example, how much detail about a specific protocol to be performed needs to be provided. Additionally, will prioritization be graded and transmitted? Will scheduling data be available to the ordering physician. Will the ordering physician be able to select an available exam slot and time at POE order placement? An adaptive workflow system is able to analyze changes to the surrounding operating environment as well as its own operations to select a new response to meet its objectives.

Figure 5:
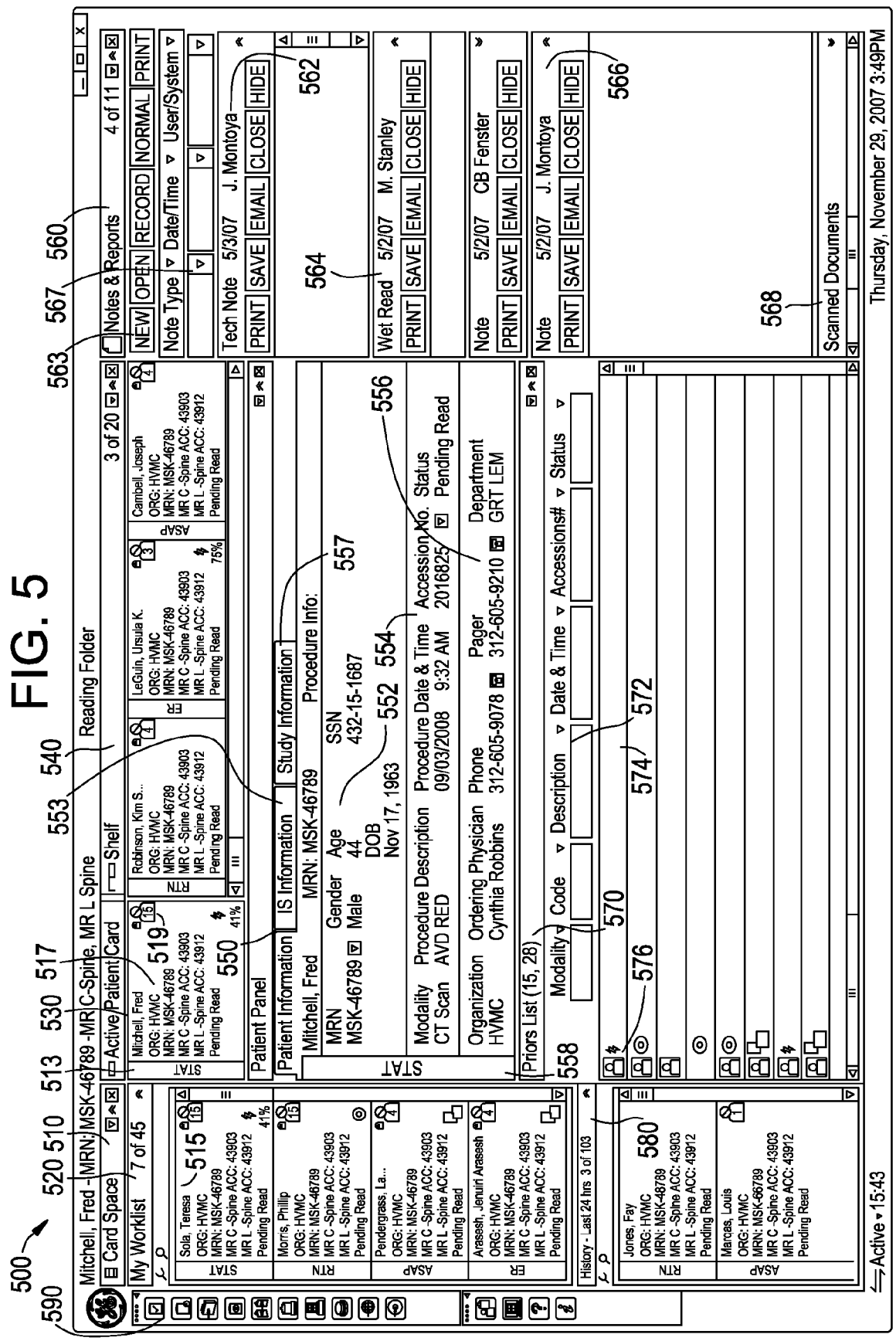
FIG. 5 depicts an example user interface providing interruption workflow management in accordance with certain embodiments of the present invention.

As discussed above, a workspace environment facilitating user workflow and easing an inconvenience of interruption can be provided in conjunction with a variety of clinical systems and processes, including clinical systems and processes discussed above. FIG. 5 depicts an example user interface or reading folder 500 providing interruption workflow management in accordance with certain embodiments of the present invention. The interface system 500 includes a patient card space 510, a worklist 520, an active patient card 530, a shelf 540, a patient panel 550, notes and reports 560, a priors list 570, a history 580, and tools 590. Components of the user interface system 500 can be implemented separately and/or in various forms of combination in hardware, software, and/or firmware, for example.

The patient card space 510 can include one or more patient cards for the user logged into the interface 500. The worklist 520 includes a list of patient cards 515 representing patients and associated tasks on the user's worklist. Each patient card 515 can include a status indicator 513, a snapshot 517 of key patient information and tasks requested, and/or one or more icons 519 providing information regarding the form of associated patient information (e.g., acquired images, lab results, dictation, etc.).

The status indicator 513 can include an alphanumeric indicator of the patient's priority and can also be color-coded to indicate a severity or priority of the patient (e.g., red for stat, orange for emergency room, yellow for as soon as possible, green for routine, etc.). In certain embodiments, patient cards 515 in the worklist 520 can be automatically organized according to status indicator 513, for example. In certain embodiments, status indicators 513 can be updated based on changing conditions, for example.

The active patient card 530 indicates which patient is currently being reviewed via the interface 500. This patient's information is displayed in the patient panel 550, the notes and reports 560, and the priors list 570, for example. In an example, a patient card 515 can be moved (e.g., by selecting and dragging) from the worklist 520 to the active patient card area 530, which results in that patient's information being propagated to the patient panel 550, the notes and reports 560, and the priors list 570.

The shelf 540 allows the user to place patient cards 515 for storage until needed again. Patient information, context, etc., can be saved on the shelf 540 in association with the patient card 515 until the user chooses to revisit that patient. In certain embodiments, information on the shelf 540 can be accessible later in time, at another workstation, by other authorized users, etc.

The patient panel 550 provides information regarding a patient for a user to review. For example, the patient panel 550 can provide patient information including patient identification and demographic information 552. The patient panel 550 can also provide recent procedure information 554 for the patient, such as modality, procedure description, procedure date and time, accession number, status, organization, etc. The patient panel 550 can also provide referring physician contact information 556, for example. The patient panel 550 can include a status indicator 558, similar to the patient card 515 status indicator 513, that can indicate via alphanumeric and/or graphical (e.g., color-based) information a degree of importance, urgency, and/or severity of the patient's review by the user. Via the patient panel 550, a user can also access clinical information system information 553 for the patient and study information 557 for the patient, for example. A user, such as a radiologist, can pull up a patient imaging study in conjunction with the workspace interface 500 to review the study and generate a report for a referring physician, for example.

Using the notes and reports panel 560, a user can review previously saved notes and/or reports and/or generate new notes and/or reports, for example. As shown, for example, in FIG. 5, various sections of the notes and reports 560 allow a user to show, print, email, close, edit, save, etc. different types of notes and/or reports. For example, the notes and reports 560 depicted in FIG. 5 provides a tech note 562, a wet read 564, and other notes 566. Notes and reports 560 can provide access to scanned documents 568 for the patient, for example. Notes and reports 560 can provide options 563 for a user to, for example, generate a new note/report, open an existing note/report, dictate a note/report, normalize, print, etc. Search and/or sorting capability 567 can be provided based on one or more criteria such as type, date/time, user/system, etc.

The priors list 570 displays and provides access to prior exams, etc., previously obtained and/or analyzed for the patient that are stored in a clinical system accessible by the interface 500. Prior information can be sorted and/or searched 572 according to one or more criteria such as modality, code, description, date/time, accession number, status, etc. Items 574 on the priors list 570 can include one or more icons 576 indicating prior study type, method of study access, etc.

The history 580 can provide patient card(s) 515 for a certain number of previously viewed patients for the user, group of users, institution, etc. As shown, for example, in FIG. 5, the history 580 includes a listing of patient cards 515 for patients seen in the last twenty-four hours. This history list 580 is scrollable and accessible by the user in case the user wishes to refer back to a previously reviewed item in his or her worklist.

One or more tools 590 can be provided to facilitate user interaction with components of the reading folder interface 500. Tools 590 can include, for example, one or more of a notes tool, a tasks tool, a search tool, a transfer tool, a print tool, a dictation tool, a help tool, etc.

In operation, for example, a user accessing the user interface 500 sees a list 520 of patients without having to go back to another workspace and can easily switch between patients by selecting a patient card 515. The patient card 515 provides the user with a summary 517 of, for example, the patient record, patient priority, patient and procedure demographics, key identification information, graphical indicator of priority, etc. Priority options 513 are defined and indicated for the patient. Icons 519 define how the study is available to the user (e.g., streamed, local availability, hard copy, and/or prefetching, etc.). Icons or other indicators can indicate whether a user has locked a workflow, whether a user has access, etc. A user can manipulate and move patient cards 51 between the worklist 520, active patient card area 530, patient card shelf 540, and history 580. Moving a patient card 515 to the active patient card area 530 results in that patient's information being provided in the patient panel 550, the notes and reports 560, and the priors list 570. The user can then use available tools 590 to manipulate the patient information; view study images, laboratory results, etc.; make notes; and the like. If an emergency patient is referred to the user, the user requests and is awaiting additional information for a patient, etc., the user can move the patient card 515 to the shelf 540 and retrieve a next patient card 515 from the worklist 520 and/or shelf 540, for example. The user can then come back to a patient card 515 on the shelf 540 and retrieve it for active display.

Figure 6:
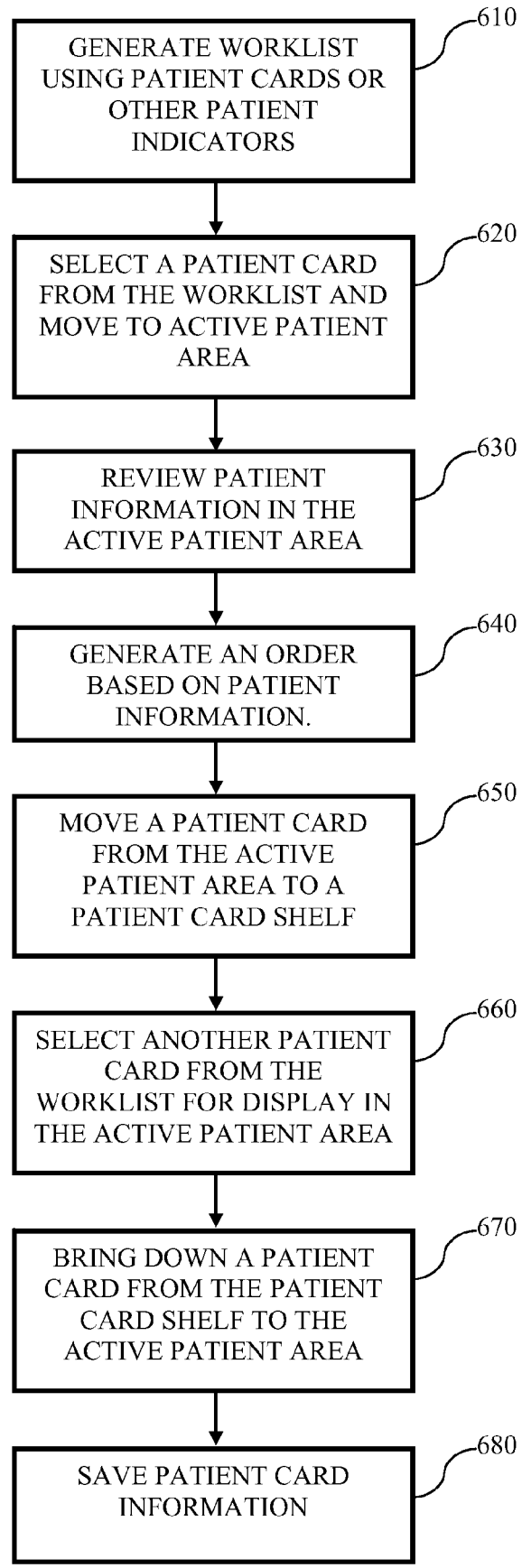
FIG. 6 illustrates a flow diagram for a method for interruption workflow management in a clinical environment in accordance with certain embodiments of the present invention.

FIG. 6 illustrates a flow diagram for an example method 600 for interruption workflow management in accordance with certain embodiments of the present invention. At 610, a user worklist is generated using a plurality of patient cards or other patient indicators. For example, a reviewing radiologist has a workspace 500 with a series of patients having image studies for his or her review, and those patients, represented by cards or similar indicators 515, can be stored in a worklist 520.

At 620, a patient card or other patient indicator is selected from the worklist and moved to an active patient area. For example, the radiologist can, using a cursor manipulation device, such as a mouse, ball, touchscreen etc., place a patient card 515 in the active patient area 530.

At 630, patient information is reviewed in the active patient area. For example, placing a patient card 515 in the active patient area 530 causes the patient's information, including access to patient image study information, to be displayed for the user.

At 640, an order can be generated based on the patient information. For example, after reviewing a patient's information and a recent image study, the reviewing radiologist can request an additional image view to be taken of the patient.

At 650, a patient card or other patient indicator is moved from the active patient area to a patient card shelf For example, while the radiologist is awaiting the additional image view, the radiologist can move that patient's card 515 from the active patient area 530 to the shelf 540 for later retrieval so that the radiologist can examine the next patient in his or her worklist 520.

At 660, another patient card or patient indicator can be selected from the worklist and placed in the active patient area. For example, the radiologist can select the next patient from his or her worklist 520 based on a criteria such as next in line, a priority or status indicator 513, etc. That patient's patient card 515 can be dragged to the active patient area 530, and the radiologist can review that patient's information via the patient panel 550, etc.

At 670, a patient card or indicator can be brought down from the patient card shelf and placed back in the active patient area. For example, once the additional view the radiologist requested for the first patient is provided to the radiologist, the radiologist can retrieve that patient's card 515 from the shelf 540 and bring it back to the active patient area 530, complete with context and status information, for example. Additional information, such as the new patient image(s), can be provided to the user via an alert on the interface 500 and/or via a separate system, for example.

At 680, patient card information can be saved. For example, changes to content, context, and/or other status information made to a patient card 515 via the patient panel 550, notes and reports 560, priors list 570, etc., can be saved in relation to the patient card 515 for later retrieval.

One or more of the steps of the method 600 may be implemented alone or in combination in hardware, firmware, and/or as a set of instructions in software, for example. Certain examples may be provided as a set of instructions residing on a computer-readable medium, such as a memory, hard disk, DVD, or CD, for execution on a general purpose computer or other processing device.

Certain examples may omit one or more of these steps and/or perform the steps in a different order than the order listed. For example, some steps may not be performed in certain examples. As a further example, certain steps may be performed in a different temporal order, including simultaneously, than listed above.

It should be understood by any experienced in the art that the inventive elements, inventive paradigms and inventive methods are represented by certain exemplary embodiments only. However, the actual scope of the invention and its inventive elements extends far beyond selected embodiments and should be considered separately in the context of wide arena of the development, engineering, vending, service and support of the wide variety of information and computerized systems with special accent to sophisticated systems of high load and/or high throughput and/or high performance and/or distributed and/or federated and/or multi-specialty nature.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for interruption workflow management via a workstation in a clinical enterprise, said method comprising:

generating, using a processor, an electronic worklist displayed for a user via a user interface, the worklist including a plurality of patients and associated patient tasks to be performed by that user, each patient represented in the worklist using a graphical patient indicator, the patient indicator visually providing patient information including a) a summary of a patient record corresponding to the patient, b) at least one task to be performed by the user with respect to the patient, and c) a status of the patient via the graphical patient indicator;

retrieving and displaying, using the processor and upon user selection of a first patient indicator from in the worklist of patient indicators, patient information associated with the first patient indicator in a first area of the user interface in response to selection of the first patient indicator from the worklist, wherein the first area is configured to process data corresponding to the first patient indicator to retrieve the patient information associated with the first patient indicator and facilitate interaction by the user with the patient information while the first patient indicator is positioned in the first area, the patient information associated with the first patient indicator to be editable based on user input while the first patient indicator is positioned in the first area;

facilitating user interaction with respect to the patient information associated with the first patient indicator displayed in the first area of the user interface while the first patient indicator remains in the first area;

facilitating movement of the first patient indicator from the first area to a second area of the user interface for later retrieval in response to a second patient indicator being designated for the first area, wherein the second area saves and maintains a) a pendency of the patient information, b) a context of user review of the first patient indicator, and c) status information regarding user interaction with the patient information for the first patient indicator while user interaction with patient information associated with the second patient indicator is facilitated via the first area; and restoring the first patient indicator from the second area to the first area in response to user input to position the first patient indicator back in the first area from the second area, wherein restoring includes restoring a) the patient information associated with the first patient indicator, b) the status of user interaction with the patient information, and c) a context of user review of the first patient indicator, saved while the first patient indicator was being held in the second area, for user interaction in the first area.

2. The method of claim 1, wherein the first patient indicator comprises an electronic patient card.

3. The method of claim 1, wherein positioning of the patient indicator in the first area triggers display of the patient information in a patient panel, a priors list, and a notes and reports area.

4. The method of claim 1, further comprising selecting a second patient indicator from the worklist to be displayed in the first area while the first patient indicator is in the second area.

5. The method of claim 1, further comprising saving modified patient information for later retrieval.

6. The method of claim 1, wherein the first patient indicator includes patient summary information.

7. The method of claim 1, wherein the first patient indicator includes a patient urgency status indicator.

8. The method of claim 1, wherein the first patient indicator includes one or more icons indicating a source and access for patient exam information.

9. An interruption workflow management system for a clinical enterprise, said system comprising:
   a processor and a memory including computer program instructions, the instructions, when executed by the processor, to implement a user interface including:
   an electronic worklist displayed for a user via the user interface, the worklist including a plurality of graphical patient indicators representing patients for which tasks are to be performed by a user, each patient indicator visually providing patient information including a) a summary of a patient record corresponding to the patient, b) at least one task to be performed by the user with respect to the patient, and c) a status of the patient via the graphical patient indicator;
   a first area displaying patient information associated with a first patient indicator selected from the worklist of patient indicators, the first area configured to process data corresponding to the first patient indicator to retrieve the patient information associated with the first patient indicator and facilitate interaction by the user with the patient information while the first patient indicator is positioned in the first area, the patient information associated with the first patient indicator to be editable based on user input while the first patient indicator is positioned in the first area; and
   a second area holding one or more patient indicators from at least one of the worklist and the first area for later retrieval in response to user input, wherein the second area is to save and maintain a) pendency of the patient information, b) a context of user review of the first patient indicator, and c) status information regarding user interaction with the patient information for a first patient indicator while a second patient indicator with associated patient information is being examined in the first area, the second area to facilitate restoration of the first patient indicator from the second area to display in the first area in response to user input, wherein restoration includes restoring a) the patient information associated with the first patient indicator, b) the status of user interaction with the patient information, and c) a context of user review of the first patient indicator, saved while the first patient indicator was being held in the second area, for user interaction in the first area.

10. The system of claim 9, wherein the patient indicator comprises an electronic patient card.

11. The system of claim 9, wherein positioning of the patient indicator in the first area triggers retrieval and display of the patient information in a patient panel, a priors list, and a notes and reports area.

12. The system of claim 9, wherein a second patient indicator is selected from the worklist to be displayed in the first area while the first patient indicator is stored in the second area.

13. The system of claim 9, wherein the patient indicator includes patient summary information.

14. The system of claim 9, wherein the patient indicator includes a patient urgency status indicator.

15. The system of claim 9, wherein the patient indicator includes one or more icons indicating a source and access for patient exam information.

16. The system of claim 9, further comprising a history of patient indicators previously examined within a predefined time period.

17. The system of claim 9, further comprising a plurality of tools for manipulation of the patient information.

18. A non-transitory machine readable storage medium having a set of instructions for execution on a computing machine, which, when executed, cause the computing machine to execute a method for interruption workflow management via a workstation in a clinical enterprise, said method comprising:
   generating an electronic worklist displayed for a user via a user interface, the worklist including a plurality of patients and associated patient tasks to be performed by that user, each patient represented in the worklist using a graphical patient indicator, the patient indicator visually providing patient information including a) a summary of a patient record corresponding to the patient, b) at least one task to be performed by the user with respect to the patient, and c) a status of the patient via the graphical patient indicator;
   retrieving and displaying, upon user selection of a first patient indicator from in the worklist of patient indicators, patient information associated with the first patient indicator in a first area of the user interface in response to selection of the first patient indicator from the worklist, wherein the first area is configured to process data corresponding to the first patient indicator to retrieve the patient information associated with the first patient indicator and facilitate interaction by the user with the patient information while the first patient indicator is positioned in the first area, the patient information associated with the first patient indicator to be editable based on user input while the first patient indicator is positioned in the first area;
   facilitating user interaction with respect to the patient information associated with the first patient indicator displayed in the first area of the user interface while the first patient indicator remains in the first area;
   facilitating movement of the first patient indicator from the first area to a second area of the user interface for later retrieval in response to a second patient indicator being designated for the first area, wherein the second area saves and maintains a) a pendency of the patient information, b) a context of user review of the first patient indicator, and c) status information regarding user interaction with the patient information for the first patient indicator while user interaction with patient information associated with the second patient indicator is facilitated via the first area; and
   restoring the first patient indicator from the second area to the first area in response to user input to position the first patient indicator back in the first area from the second area, wherein restoring includes restoring a) the patient information associated with the first patient indicator, b) the status of user interaction with the patient information, and c) a context of user review of the first patient indicator, saved while the first patient indicator was being held in the second area, for user interaction in the first area.

* * * * *